United States Patent [19]

Paolini et al.

[11] Patent Number: 5,621,392
[45] Date of Patent: Apr. 15, 1997

[54] FLOW DETECTOR

[75] Inventors: Francesco Paolini, Cosenza; Marco Paraluppi, Medolla; Luca Vinci, Poggio Rusco Mantova, all of Italy

[73] Assignee: Hospal Ltd., Basel, Switzerland

[21] Appl. No.: 546,733

[22] Filed: Oct. 23, 1995

Related U.S. Application Data

[63] Continuation of Ser. No. 81,330, filed as PCT/EP92/02457, Oct. 28, 1992, abandoned.

[30] Foreign Application Priority Data

Nov. 5, 1991 [IT] Italy .................. TO91A0834

[51] Int. Cl.⁶ .................................. G08B 21/00
[52] U.S. Cl. .................. 340/608; 340/609; 128/DIG. 13
[58] Field of Search .................. 340/608, 609, 340/606; 128/DIG. 12, DIG. 13; 604/67, 31, 65, 192; 73/861.06, 861.41

[56] References Cited

U.S. PATENT DOCUMENTS

| | | | |
|---|---|---|---|
| 3,609,379 | 9/1971 | Hildebrandt | 128/DIG. 13 |
| 3,768,084 | 10/1973 | Haynes | 340/608 |
| 4,314,484 | 2/1982 | Bowman | 73/861.41 |
| 4,321,461 | 3/1982 | Walter, Jr. et al. | 340/608 |
| 4,509,943 | 4/1985 | Hanzawa | 128/DIG. 13 |
| 4,720,636 | 1/1988 | Benner, Jr. | 128/DIG. 13 |
| 4,946,439 | 8/1990 | Eggers | 128/DIG. 13 |
| 5,103,827 | 4/1992 | Smith | 128/DIG. 13 |
| 5,166,667 | 11/1992 | Jen | 128/DIG. 13 |
| 5,256,155 | 10/1993 | Yerlikaya et al. | 128/DIG. 13 |
| 5,267,978 | 12/1993 | Dirr, Jr. | 128/DIG. 13 |

FOREIGN PATENT DOCUMENTS

| | | |
|---|---|---|
| 0229354 | 7/1987 | European Pat. Off. . |
| 2920693 | 12/1980 | Germany . |
| WO86/03597 | 6/1986 | WIPO . |

*Primary Examiner*—Jeffery Hofsass
*Assistant Examiner*—Benjamin C. Lee
*Attorney, Agent, or Firm*—Finnegan, Henderson, Farabow, Garrett & Dunner, L.L.P.

[57] ABSTRACT

A liquid flowed detection system is disclosed for monitoring continuous and discontinuous liquid flow in a fluid circuit. The system includes a holding device for maintaining a drip chamber so that its elongated axis generally lies in a vertical plane. A light emitter is oriented to transmit light along an optical path through the drip chamber and intersecting its elongated axis. A light detector located in the optical path opposite the light emitter, generates a signal representative of light received from the light emitter. A processor receives information from the detector and generates a control signal representative of a variability over time of the light detector signal. When the control signal drops below a predetermined level, a flow absence signal is generated which is then correlated to the system's pump velocity corresponding to a time interval (T). If the flow absence signal occurs continuously in a comparison time interval (T), a warning signal is generated.

13 Claims, 2 Drawing Sheets

5,621,392

FLOW DETECTOR

This application is a continuation, of application Ser. No. 08/081,330, filed as PCT/EP92/02457, Oct. 28, 1992, now abandoned.

BACKGROUND OF THE INVENTION

1. Field of the Invention

The present invention relates to a liquid flow detector of the type associated with a drip chamber formed by a transparent cup-shaped container. An inlet tube extends into the drip chamber and includes a nozzle disposed in the upper portion of the container. The liquid collected in the container flows from the base of the container via an outlet tube under the action of a peristaltic pump disposed in the outlet tube.

2. Description of the Related Art

Detectors of known type are applied to drip chambers and detect the flow of liquid by means of optoelectronic sensors which comprise a photoemitter and a photodetector defining an optical path which intersects the flow of liquid. Flow detectors of known type also comprise an electronic unit which receives as input the signal supplied by the photodetector in order to ascertain whether the liquid is flowing into the container.

Moreover, detectors of known type are separated into two classes depending on the characteristics of the liquid flow (continuous or in droplets). In the first crass of detectors of digital type, the electronic unit counts the number of pulses of the input signal (caused by the droplets falling from the nozzle) in order to ascertain the quantity of liquid flowing into the container. The first class of detector is not able to monitor the flow of liquid when it is continuous as the pulses of the input signal are missing.

In the second class of detectors of analog type, the electronic unit dectects the amplitude of the input signal which is a function of the quantity of liquid falling from the nozzle and compares it with a reference level in order to measure the flow of this liquid. This second class of detector is highly influenced by the characteristics of the container and the condition of the sensor and provides an incorrect reading when the container has yellowed because of wear or age. The presence of vapours in the container may also have an adverse effect on the measurement.

SUMMARY OF THE INVENTION

An object of the present invention is to provide a flow detector which resolves the drawbacks of known detectors.

This object is achieved by the present invention which relates to a liquid flow detector which may be used in conjunction with a transparent container interposed along a duct, this detector comprising a first transducer associated with the container and intersecting a path along which the flow of liquid takes place so as to generate an electrical signal correlated with this flow, characterized in that it comprises processing means associated with the first transducer in order to generate a control signal as a function of the variation over time of the signal generated by the first transducer and comparison means-for comparing this control signal with a reference value and generating a signal indicating an absence of flow.

BRIEF DESCRIPTION OF THE DRAWING

The invention is described with references to the accompanying drawings, in which.

DETAILED DESCRIPTION OF THE PREFERRED EMBODIMENTS

Figure 1:
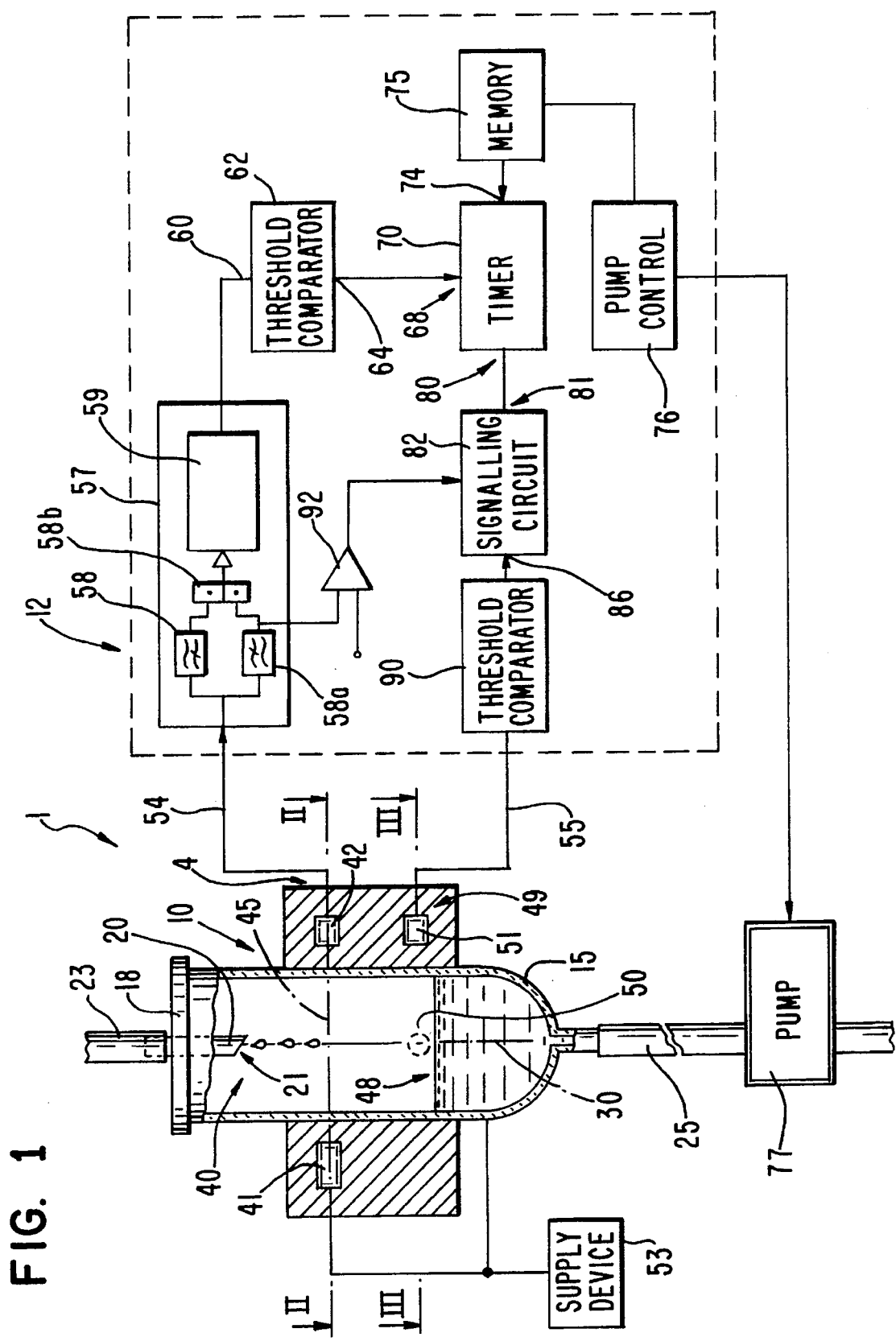
FIG. 1 is a schematic diagram of in outline, a flow sensor comprising a unit and a probe associated with a drip chamber and a control circuit in accordance with the present invention.

In FIG. 1, a flow detector is generally depicted by reference numeral 1 and comprises a probe 4 which is operationally associated with a drip chamber 10 into which a liquid flows and an electronic unit 12 including a control circuit.

The drip chamber 10 is in particular formed by a tubular cup-shaped container 15 which is made from transparent plastic and is closed at the top by a plane stopper 18 traversed by a nozzle 20 provided with an inclined end edge 21 contained within the drip chamber 10. The nozzle 20 communicates with an inlet tube 23 within which the liquid flows.

The container 15 is also connected at the bottom to an outlet tube 25 which extends from a base wall of the container 15 and is connected to a pump 77.

The container 15 is disposed vertically with respect to a horizontal plane and the liquid discharged from the nozzle 20 drops along a vertical path 30 and is collected in a base portion of the container 15.

Figure 2:
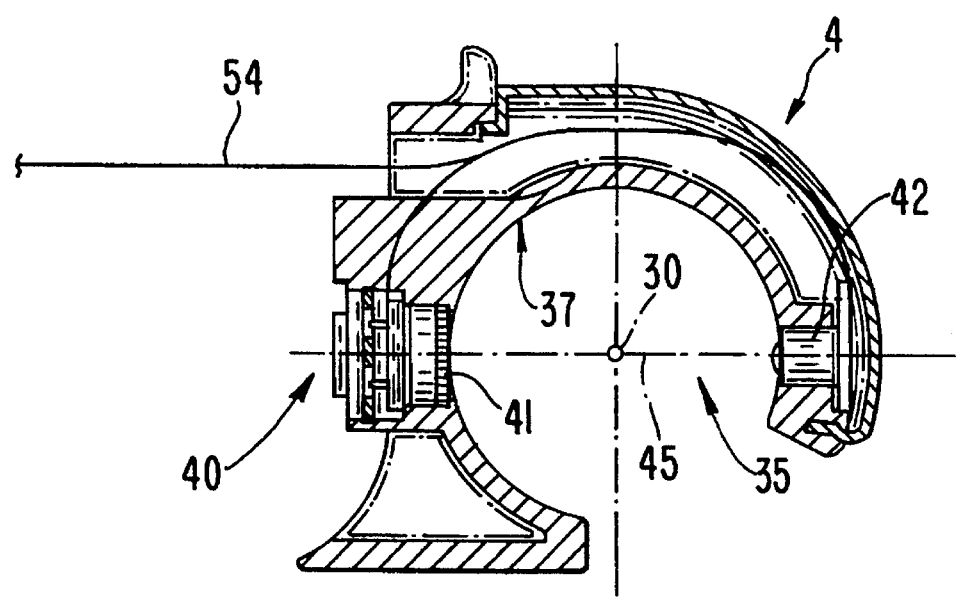
FIG. 2 is a first cross-section through the probe of FIG. 1.
Figure 3:
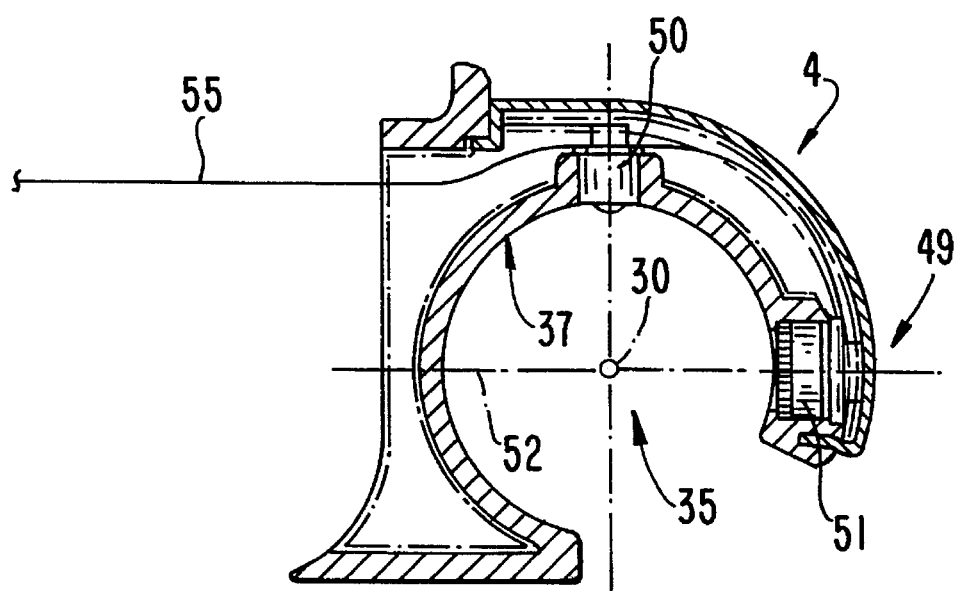
FIG. 3 is a second cross-section through the probe of FIG. 1.

The probe 4 (FIGS. 2 and 3) has a groove 35 which is limited by a cylindrical wall portion 37 and houses a central portion of the container 15 which is disposed in contact with the wall 37.

The probe 4 houses a first optoelectronic transducer 40 comprising a photoemitter 41 (for instance and LED diode) and a photodetector 42 (for instance a phototransistor) disposed on opposite sides of the wall 37 so as to define an optical path 45 passing through the container 15 and intersecting the path 30.

The probe 4 houses a second optoelectronic transducer 49 disposed below the transducer 40 at a distance from the base of the container such that, in normal operating conditions of the liquid flow system (correct flow velocity), the free surface 48 of the liquid housed in the lower portion of the container 15 is disposed below the transducer 49. The transducer 49 comprises a photoemitter 50 (for instance an LED diode) and a photodetector 51 (for instance a phototransistor) disposed perpendicular to one another. Consequently, in normal conditions, the rays generated by the photoemitter 50 are propagated along a cone of light with an opening angle such that they strike the photodetector 51. In contrast, when the liquid level in the container 15 is high and reaches the transducer 49, the attenuation of the light by the liquid and the restriction of the light cone prevent the light rays generated by the photoemitter 50 from reaching photodetector 51 which then generates a corresponding electrical signal.

The transducer 42 and 49 are supplied by a supply circuit 53 and are connected to the unit 12 by respective lines 54 and 55. The unit 12 comprises a unit 57 which receives as input the signal from the photodetector 42 and generates, in a manner which will be explained in detail below, a control signal representative of the variability over time of the signal from the photodetector 42. This control signal is supplied to an input 60 of a comparator circuit 62 which has an output 64 connected to a first input 68 of a timer circuit 70.

The circuit 70 has a second input 74 connected to a memory 75 coupled to a pump control circuit 76 which is associated with the pump 77 of a fluid circulation plant (not shown) generally of the roller type.

The circuit 70 also has an output 80 which is connected to a first input 81 of a signalling circuit 82 having a second input 86 connected to a threshold comparator circuit 90. The threshold comparator circuit 90 receives the signal generated by the photodetector 51 as input.

In use, the liquid from the tube 23 falls under the effect of gravity from the nozzle 20 along the path 30, passing through the optical path 45, and is collected on the base of the container 15. In this way, the signal generated by the photoemitter 41 is modulated by the liquid flowing from the nozzle 20 and the signal obtained by the photodetector 42 is variable over time as a function of the flow of fluid along the path 30.

The signal generated by the photodetector 42 is variable over time only in the presence of a flow of liquid, since if the liquid falls in the form of droplets this signal has a pulse component due to the interruption of the optical path 45 caused by the droplets and if the liquid falls continuously this signal has a variable component over time due, on the one hand, to small momentaneous variations in flow because of the shape of the edge 21 and the surface tension of the liquid and, on the other hand, to the turbulence of the liquid falling from the nozzle 20, with the result that the index of refraction of the liquid varies in time and space.

The unit 57 generates a control signal which is proportional to the variability of the input signal.

For this purpose, the unit 57 comprises a high-pass filter 58, a low-pass filter 58a and a divider circuit 58b connected at its output with the input of a block 59. The filters 58a and 58 in particular have respective inputs connected with the line 54 and outputs connected with the divider circuit 58b so that the signal from the filter 58 is divided by the signal from the filter 58a and the signal produced by this division is supplied to the circuit 59.

In practice, the filter 58 eliminates the continuous component of the signal received by the unit 57 so as to keep solely the alternating component due to the pulses generated by the droplets or by the variations of flow and index of refraction in the case of a continuous flow.

This alternating component is then divided by the mean value of the signal received as output from the filter 58a so as carry out a "standardization" of this alternating component. This operation is carried out in order to make the signal at the input of the circuit 59 independent of the amplitude of the signal generated by the photodetector 42, preventing, for example, variations of the signal level due to the aging of the photoemitter or the yellowing of the walls of the container 15 from affecting the operation of the unit 57.

The standardized alternating component output from the block 58b is then supplied to the block 59 which, for instance, calculates its mean quadratic value in order to eliminate disturbances and reduce the incidence of errors, and is then supplied to the circuit 62 in order to generate a flow absence signal when the control signal drops below a predetermined reference level.

The reduced size of the control signal is representative of an absence of flow along the path 30.

The flow absence signal is then supplied to the circuit 70 which processes it in order to correlate it with the flow velocity of the liquid determined by the velocity of the pump 77.

The circuit 70 in particular checks whether the flow absence signal is present continuously in a comparison time interval T, whose duration is smaller in the case of a high velocity of the pump 77 (and therefore a high liquid flow) or greater in the opposite case, and activates the circuit 82 if the result of this comparison is positive.

This check is carried out since the variability of the signal input to the unit 57 is, to some extent, correlated with the flow velocity of the liquid with the result, in the case of a discontinuous flow of droplets (with a few droplets per minute), that the flow absence signal may be generated because in this case the liquid flow is zero in the time intervals between two successibe droplets.

Consequently, if the pump is operating at a low number of revolutions corresponding to a flow of liquid in droplet form, the flow absence signal may be present in the time intervals between the droplets.

The flow absence signal is therefore monitored over a broad time interval since the circuit 82 is actuated only if the flow absence signal is present throughout the time interval showing that no droplet has fallen during the whole of the time T.

If the pump 77 is operating at a high number of revolutions corresponding to a high liquid flow, the absence of the control signal shows a malfunction as the liquid flow, which should be high, is in practice zero.

This situation must be detected immediately because of the risks entailed, with the result that in this case the time interval during which the flow absence signal is generated by the comparator 62 is small. The time interval T is preferably selected from three different values, stored in the memory 75, corresponding to three different velocity intervals of the pump 77.

The flow absence signal which may have been generated by the timer 70 is then supplied to the signalling circuit 82 which generates a corresponding acoustic and/or optical signal to warn the operator of the absence of flow.

The unit 12 further comprises a comparator circuit 92 which has a first input connected to the output of the block 58a, a second input disposed at a reference potential close to zero and an output connected to the circuit 82.

The circuit 92 actuates the circuit 82 when its first input is at a voltage close to zero showing the absence of an input signal in the block 57 (due, for instance, to a malfunction of the photodetector 42).

The circuit 92 further prevents, in the absence of an input signal to the block 57, the divider block 58b from carrying out inadmissible operations, for instance the division of zero by zero whose result would be completely without significance.

The transducer 49 carries out the auxiliary function of monitoring the level of the liquid contained in the container 15 in order to disable the signalling circuit 82 when the free surface 48 of the liquid has reached the transducer 49. In this case, the liquid, because of disturbances due for instance to the pump 77, may interfere with the optical path 45 making detection by the transducer 40 impossible or unreliable.

If the liquid contained in the container 15 interferes with the optical path 52, the light generated by the photoemitter 50 no longer reaches the photodetector 51 which consequently does not transmit any output signal. The comparator circuit 90 which compares the output of the photodetector 51 with a reference level close to zero consequently detects this absence of signal and supplies a corresponding overflow signal to the alarm signalling circuit 82. This circuit 82 consequently disregards any alarm signal generated-by the timer 70 and generates a malfunction signal.

It is clear from the above that the flow detector of the present invention resolves the drawbacks of known detectors. This detector is not sensitive to the level of the signal supplied by the photodetector but is sensitive to the variation of this signal over time; this prevents errors due to the variation of the signal level (due to the yellowing of the container or the presence of vapours).

The flow detector also makes it possible to control the flow of blood in various operating conditions (flow in the form of droplets or as a continuous flow) as a function of the liquid flow detected by measuring the velocity of the pump.

It is also clear that modifications and variants may be made to the present invention without departing from the scope of protection of the invention.

The unit 57, for instance, could comprise blocks differing from those described and could process the signal generated by the photodetector 42 in a different way. The block 59, for instance, could be replaced by a block adapted to calculate the absolute value of the standardized alternating component in order to eliminate disturbances and reduce the incidence of errors.

The transducer 49 could be of a type differing from that described, for instance comprising an ultrasound sensor.

What is claimed is:

1. A liquid flow detection system for monitoring continuous and discontinuous liquid flow in a fluid circuit including a container flow-connected to a variable velocity pump, the system comprising:

a holding device for maintaining the container so that an elongated axis of the container generally lies in a vertical plane;

a light emitter oriented to transmit light along an optical path through the container and intersecting the elongated axis of the container;

a light detector located in the optical path opposite the light emitter, the detector for generating a signal representative of light received from the light emitter;

processing means for receiving the light detector signal and for generating a control signal representative of a variability over time of the light detector signal;

means for generating a flow absence signal when the control signal drops below a predetermined level;

means for receiving a pump velocity signal corresponding to the variable velocity of the pump;

means for correlating the flow absence signal with the pump velocity signal; and means for signaling when the flow absence signal is present continuously in a comparison time interval (T) corresponding to the pump velocity signal.

2. The system of claim 1, wherein the correlating means includes means for storing a plurality of preset comparison time intervals (T), means for selecting a specific comparison time interval (T) with respect to an actual velocity of the pump, and means for checking whether the flow absence signal is present continuously in the specific comparison time interval (T).

3. The system of claim 1 wherein the comparison time interval (T) has a duration which is inversely proportional to said pump velocity indicative of the flow velocity of liquid in the circuit connected to the container.

4. The system of claim 1, wherein the processing means includes a high pass filter for receiving the light detector signal and for outputting a high pass signal therefrom, a low pass filter for receiving the light detector signal and for outputting a low pass signal therefrom, dividing means for dividing the high pass signal by the low pass signal and generating a resultant signal independent of an amplitude of the light detector signal, and means for eliminating disturbances from the resultant signal.

5. The system according to claim 4 further including means for comparing the low pass signal with a reference potential close to 0.

6. The system of claim 4 wherein the means for eliminating disturbances includes means for calculating a mean quadratic value of the resultant signal.

7. The system of claim 4 wherein the means for eliminating disturbances includes means for calculating an absolute value of the resultant signal.

8. The system of claim 1 wherein the container is a drip chamber.

9. The system of claim 8 wherein the drip chamber includes a nozzle having an inclined edge proximate an inlet end thereof.

10. The system of claim 1 further including a high liquid level transducer oriented to detect when a liquid level in the container reaches a predetermined level.

11. The system of claim 10 further including means for disabling the signaling means in response to a high liquid level signal generated by the high liquid level transducer.

12. The system of claim 10 wherein the high liquid level transducer includes a photo-emitter and a photo-detector, the photo-emitter and photo-detector being disposed along axes perpendicular to one another.

13. A liquid flow detection system for monitoring continuous and discontinuous liquid flow in a fluid circuit in which there is located a container flow-connected to a variable velocity pump, the system comprising:

a holding device for maintaining a container so that an elongated axis of the container generally lies in a vertical plane;

a first light emitter oriented to transmit light along an optical path through the container and intersecting the elongated axis of the container;

a first light detector located in the optical path opposite the light emitter, the first detector for generating a signal representative of light received from the first light emitter;

a processing circuit for receiving the first light detector signal and for generating a first control signal representative of a variability over time of the first light detector signal;

a circuit for generating a flow absence signal when the control signal drops below a predetermined level;

a second light emitter located beneath the first light emitter, relative to the vertical plane;

a second light detector oriented to receive light emitted by the second light detector, and for generating a high liquid level signal;

a circuit for receiving a pump velocity signal corresponding to the variable velocity of the pump;

a circuit for correlating the flow absence signal with the pump velocity signal;

a circuit, including a warning device, for warning when the flow absence signal is present continuously during a period of significant pump activity; and a circuit for disabling the warning device when the second light detector detects a high liquid level in the container.

* * * * *